(12) United States Patent
Grant

(10) Patent No.: US 9,592,084 B2
(45) Date of Patent: Mar. 14, 2017

(54) FOOT BEAM INSERT

(76) Inventor: William P. Grant, Virginia Beach, VA (US)

( * ) Notice: Subject to any disclaimer, the term of this patent is extended or adjusted under 35 U.S.C. 154(b) by 0 days.

(21) Appl. No.: 13/219,039

(22) Filed: Aug. 26, 2011

(65) Prior Publication Data

US 2012/0053639 A1 Mar. 1, 2012

Related U.S. Application Data

(60) Provisional application No. 61/377,684, filed on Aug. 27, 2010.

(51) Int. Cl.
*A61B 17/86* (2006.01)
*A61B 17/56* (2006.01)

(52) U.S. Cl.
CPC ...... *A61B 17/864* (2013.01); *A61B 2017/561* (2013.01)

(58) Field of Classification Search
CPC ..... A61B 17/84; A61B 17/86; A61B 17/8625; A61B 17/863; A61B 17/8635; A61B 17/864; A61B 17/8645
USPC ..... 606/62–68, 300–321, 323, 331; 411/337, 411/383
See application file for complete search history.

(56) References Cited

U.S. PATENT DOCUMENTS

| 4,697,969 A * | 10/1987 | Sparkes ............ F16B 25/0015 411/387.7 |
| 2001/0049528 A1* | 12/2001 | Kubota ............... A61B 17/742 606/65 |
| 2005/0065521 A1* | 3/2005 | Steger .................... A61B 17/80 606/281 |
| 2005/0277940 A1* | 12/2005 | Neff ............................... 606/73 |
| 2006/0036248 A1* | 2/2006 | Ferrante ............ A61B 17/7225 606/64 |
| 2007/0233123 A1* | 10/2007 | Ahmad ................ A61B 17/863 606/307 |
| 2007/0270839 A1* | 11/2007 | Jeon .................... A61B 17/7032 606/328 |
| 2008/0249579 A1* | 10/2008 | Taylor .................. A61B 17/863 606/317 |
| 2009/0157078 A1* | 6/2009 | Mikol .................. A61B 17/864 606/62 |
| 2009/0187194 A1* | 7/2009 | Hamada ........................ 606/104 |
| 2010/0211113 A1* | 8/2010 | Olson ................ A61B 17/8625 606/301 |

FOREIGN PATENT DOCUMENTS

WO  WO 2010091242 A1 * 8/2010 ........... A61B 17/744

OTHER PUBLICATIONS

Grant, William, DPM, FACFAS; "Beaming of the Charcot Midfoot"; 2016.*
Compress Compression Screw; brochure, 4 pages.
Compress Compression Screw; brochure; 1 page.

* cited by examiner

Primary Examiner — Kevin T Truong
Assistant Examiner — Tracy Kamikawa
(74) Attorney, Agent, or Firm — Alan W. Cannon

(57) ABSTRACT

The present invention is directed to a foot beam insert. The beam is a cannulated beam having a chamber defined by the hollow space inside the beam. The beam includes holes along the length of the beam that communicate between the hollow chamber inside and the outside of the beam. The beam further includes a groove or grooves in the outside surface of the beam.

10 Claims, 4 Drawing Sheets

FOOT BEAM INSERT

This application claims the benefit of U.S. Provisional Application No. 61/377,684, filed Aug. 27, 2010, which is incorporated by reference in its entirety.

The present invention is directed to a beam insert for use in foot reconstruction surgery.

BACKGROUND

Currently, charcot reconstruction surgery is based on a combination of internal and external fixation of a patient's damaged foot. The specific type of internal fixation usually revolves around the use of large diameter, cannulated hip screws—typically 6.5 mm diameter. These screws are often made out of titanium. Other metals may be used, but titanium is usually chosen because of its biocompatibility.

The problems that may occur with known methods of internal fixation include the following:

1. Charcot joints often fail to fuse; therefore, the screws, instead of compressing arthodesis sites, end up acting as load bearing members as long as the patient lives. Because of this, there exists a significant screw failure rate. That is, the screws may simply break, usually at the thread runout at the end of the screw where it resides in the midtarsal bones. The bending moments are the highest at the midtarsal joints exceeding 120,000 PSI; hence, the screw metal is insufficient for a long term 2× safety factor with commonly-used 6.5 mm titanium screws.

2. The heads of commercially available screws can tear the head of a patient's metatarsal bone, often causing infection and creating a need to remove the screw, resulting in poor outcome.

3. Similarly, the lateral column of the foot requisitely needs to be stabilized in charcot, to correct and maintain subluxation/dislocation at the articulation between the metatarsal base 4/5 and the cuboid. The dislocation of this lateral column with the cuboid coming down through the bottom of the foot can cause an essentially untreatable plantar lateral diabetic ulcer. The screws currently commercially available do not take into account the anatomy of the flaring metatarsal bases. Also they can have a head design that could potentially wedge itself into place locking this column.

4. No current screw has any surface on it that can grow into the bone, making it a true load sharing device with the bone. Instead, the screws often loosen and become a concern for infection.

SUMMARY

Accordingly, it is an object of the present invention to overcome the foregoing problems that exist with known screws and internal fixation methods. As described herein, the beam insert of the present invention is a cannulated beam. The beam includes a threaded tip. Additionally, along the length of the beam there are fluted cuts along the outside surface. The hollow beam also has porous holes along its length to allow therapeutic agents to be loaded into the inside of the hollow beam where the material may then flow out into the adjacent area of the bone which is being fixed by the beam.

DETAILED DESCRIPTION

Figure 1:
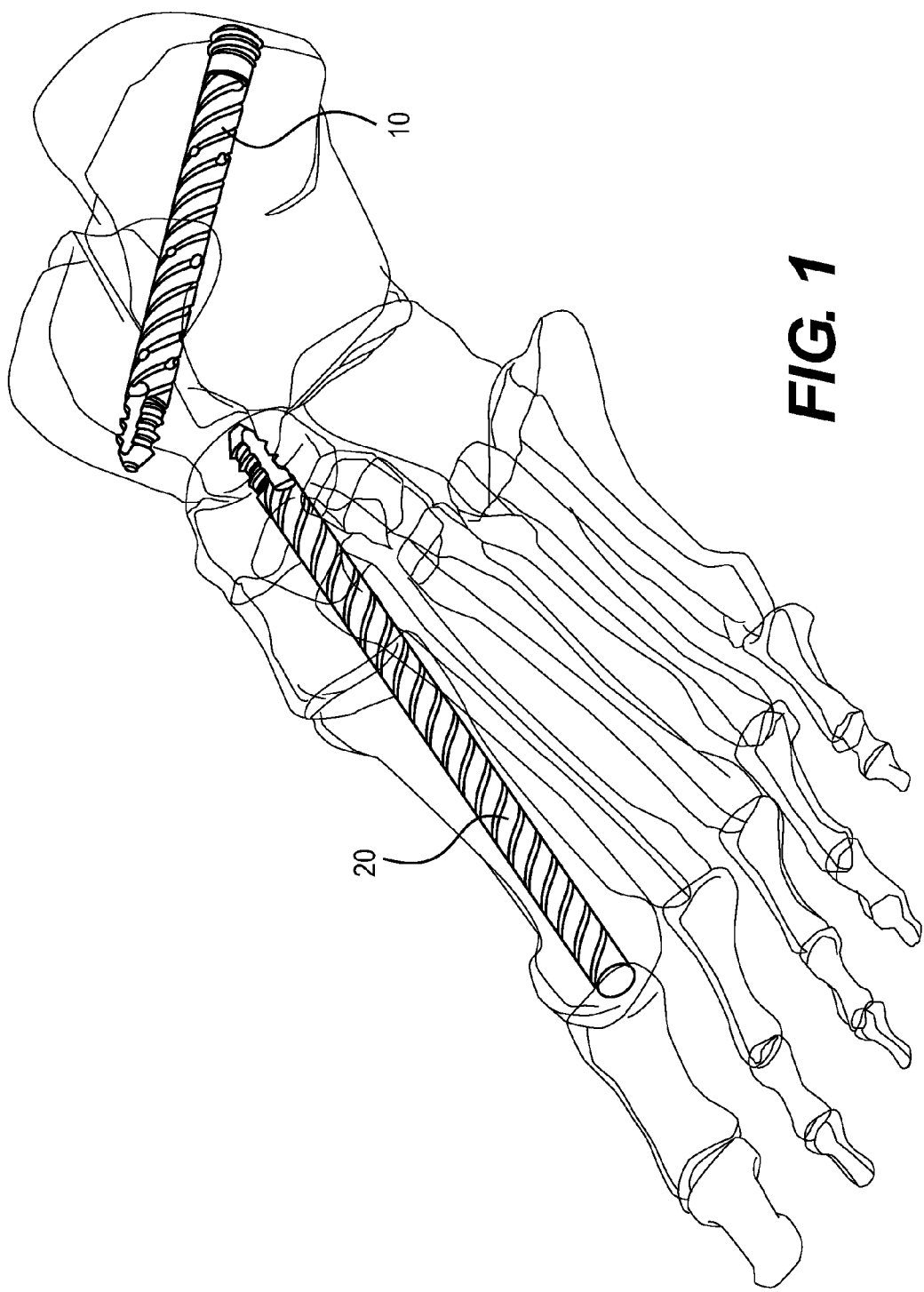
FIGS. 1 and 2 are perspective views of beams according to the present invention as they would be inserted in the bones of a patient.

The design for the beam described herein supports the arches of a collapsed foot. Special features of the insert include the design as a beam, not a screw. A screw holds two bones or bone fragments together, but a beam accepts loads of tension and compression along a bone joint construct in the foot, sharing these loads with the bones of the arch and their respective tendons and ligaments. Furthermore, the threads of a screw, by their physical nature, weaken the strength of a screw in the context of especially bending moment strength. It is desirable that most of the diameter of the beam contributes to bending strength rather than threads.

The special threaded tip of the beam pulls the beam into the cannulation hole in a patient's foot bones, potentially without drilling, and the fluted groove along the length of the beam encourages ingrowth of bone. The hollow beam has holes along its length that communicate between the chamber inside the hollow beam and the outside surface of the beam to allow a surgeon to fill the chamber with stem cells/autologous growth factors/antibiotics that can exit the holes and seep into a bone along the course of the beam influencing changes and healing in the bone. A cap applied at the end may increase pressure in the chamber inside the beam to force the cells out of the central chamber into the bone through the holes.

The new beam design takes into account a patient's foot bending moment calculations in order to select the correct size of the beam for a particular patient. For instance, for a size 11 foot/300 lb. patient for a 2× safety factor, the beam should have a 19 mm cannulation and be 7.3 mm diameter. The beam may be made of surgical stainless steel or other compatible metals. The average patient of all weights, shapes and sizes can usually accommodate a 7.3 mm beam and smaller feet and less weight will decrease the load the beam sees.

A beam may be formed of different materials. The tensile strength of materials varies: surgical stainless steel has a yield at 240,000 PSI, therefore a beam to support the medial arch of a 300 lb diabetic patient could be 7.4 mm diameter and cannulated. For titanium, the yield is 180,000 PSI; therefore, the cannulated beam for the same patient would have to be over 10 mm diameter, and would not fit in a metatarsal bone; hence the beam for such an application should be stainless. Other materials may be used following a similar calculation for suitability.

The tip of the beam should have minimal thread runout, just at the tip. This threading simply anchors the tip in the bone and prevents the beam from coming out after insertion in the bone. There should be no threads where the substantial bending moments are at the mid-tarsal joints, generally in the body portion of the beam. It is advantageous that the unthreaded body of the beam spans these joints.

The cap end of the beam may be low profile for the inner core of the first metatarsal head to preclude microfractures that lead to wound issues and loss of integrity. Conversely, the cap end of the beam may alternatively act as a larger interference screw at the lateral metatarsal bases, locking it in place as a permanent load sharer to prevent redislocation at this level. To reduce or prevent loosening, a spiral cut rough surface promotes boney ingrowth. As is evident, different cap geometries may be employed to accomplish different therapeutic purposes.

In one example, the beam described herein is also a delivery vessel for a variety of therapeutic factors that could be delivered through cannulation holes from within the chamber in the hollow beam. The factors include the following:

a. Platelet derived growth factors;
b. Stem cells; and
c. Antibiotics (particularly when treating a postoperative infection and a procedure is refixating with a new beam, the new beam can be loaded with antibiotics allowing them to seep into the bone during the perioperative period).

Figure 2:
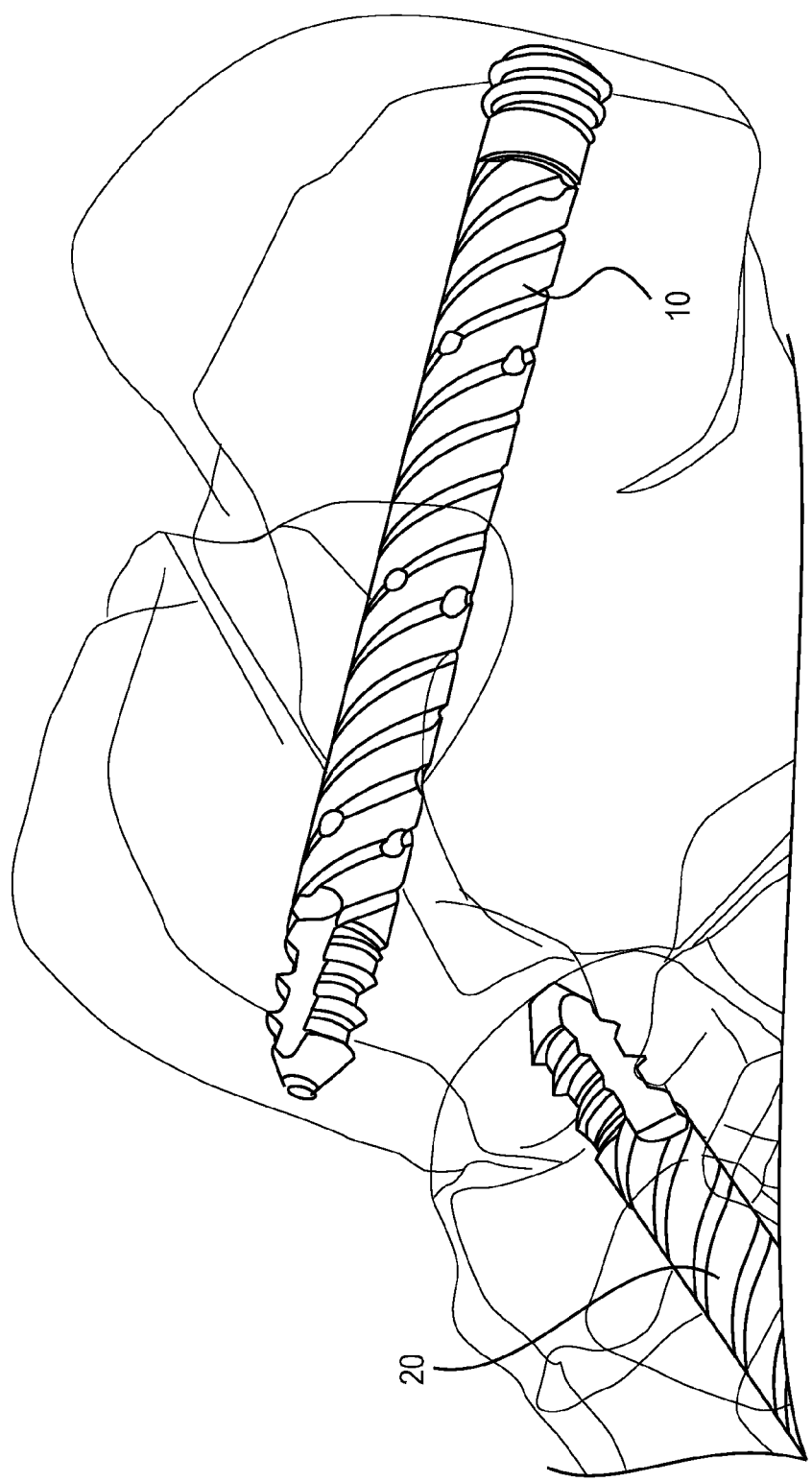

Turning now to an example of the present beam insert, FIGS. 1 and 2 are perspective views of a foot having different sized (different length) beams 10 and 20 inserted in the context of the bones of a hypothetical patient. The first beam 10 crosses the calcaneus into the talus through the subtalor joint. The second beam 20 is mounted through the medial column of the foot. Charcot typically results in fracture dislocation and collapse of the 1st metatarsal-cuneiform joint or the talar-navicular joint. When these fracture dislocations occur the bones slip through the bottom of the foot causing huge, non treatable ulcerations which have often led to amputation of the limb. Small screws or plates traditionally used to fixate these fracture dislocations often simply fail/break because they are too small and weak to hold these joints together, and when surgery is performed to try to fuse these joints, the result is often pseudoarthrosis. The second beam 20 shown transverse the 1st metatarsal medial cuneiform, navicular and talus, is buried deep in the body of the talus.

This is a beam not a screw. The intent of a screw in orthopedics is to compress a fracture or arthrodesis site in order to obtain healing of the fracture or arthrodesis of the fusion site. This is accomplished in part by the screw threads in a treated bone. The intent of the beam is to share the load of weightbearing across the arch with the bones, joints and stabilizing ligaments and to compensate for the aberration in joint integrity and ligament integrity and bone strength witnessed in charcot diabetic foot. The intent is for the beam not to fuse the joints (although they may fuse especially with the platelets). As such, the goal is to be thick and strong enough to absorb the load of weight bearing and not fail even if fusion never occurs. By growing into the bone, the beam shares the load more effectively. The specific length and diameter of the beams 10 and 20 will depend on the calculation of appropriate bending moment needs of a given patient. In very crude terms, a larger patient with a larger foot will require a longer and wider diameter beam than a relatively lighter patient having a relatively shorter foot.

Figure 3:
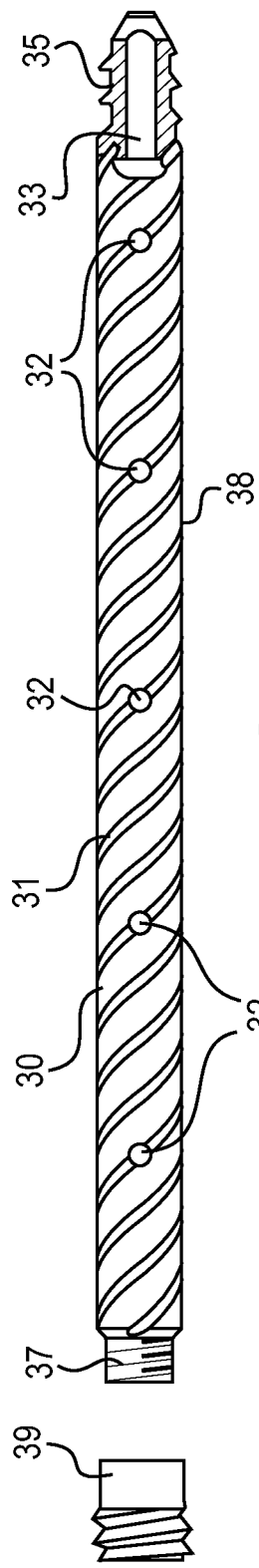
FIG. 3 is a side view of a beam as described herein.

FIGS. 3-6 are drawings of examples of beams described herein. In FIG. 3, the beam 30 has a length of 110 mm and a diameter of 7.3 mm. Specifically with reference to FIG. 3, there is shown the beam 30. The beam 30 has a spiral groove 31 carved into the outer surface of the beam 30. This groove 31 allows for bony ingrowth after a beam 30 is implanted into a patient. Additionally, the beam 30 is hollow as shown by the chamber 33 that is inside and runs the length of the beam 30. Holes or apertures 32 create a free flow or access between the inside chamber 33 and the outside surface 38 of the beam 30. It is intended that a variety of therapeutic factors could be placed in the chamber 33 that are then allowed to flow through the holes 32. The beam 30 has a threaded end 35 that is used to fix the front of the beam into the bony tissue of a patient, thereby fixing the location of the beam without having a fully threaded pin. Finally, a cap 39 is shown that mounts on the threaded cap end 37 of the beam that is opposite the tip end 35. The cap 39 has interior threads and can be placed onto the beam 30 once the therapeutic material is placed inside the chamber 33 in the beam to seal the material therein.

It should be noted that the surface 38 of the beam 30 is substantially solid and smooth such that a side view shows a mostly straight line. This is contrasted with the rough and deep ridges of threads in a screw. On the beam 30, the groove 31 is relatively shallow. Other similar roughness or unevenness could be engineered on the surface 38 as long as the roughness or unevenness does not meaningfully compromise the bending strength of the beam.

Also, the groove 31 may be fluted. That is, the side view of the groove 31 may be cut back into the beam to enhance the ingrowth effect of healing after the beam is inserted in a foot. Different fluted geometries may be adopted to facilitate the boney ingrowth.

As noted earlier herein, the beam 30 may be constructed of titanium. It is believed that surgical stainless steel is stronger than titanium. Other metallic or composite materials may alternatively be used to construct the beam 30.

Still referring to FIG. 3, the holes 32 are shown spaced relatively evenly along the length of the beam 30 on the side of the beam. There can be other holes spaced evenly with the side holes 32 as shown. The holes 32 could alternatively spaced asymmetrically along the length of the beam 30. Still further, the holes 32 can be strategically positioned to correspond to a particular portion of a patient's foot or bone structure so that the therapeutic material placed in the chamber 33 of the beam 30 will be delivered exactly where it is needed.

Figure 4:
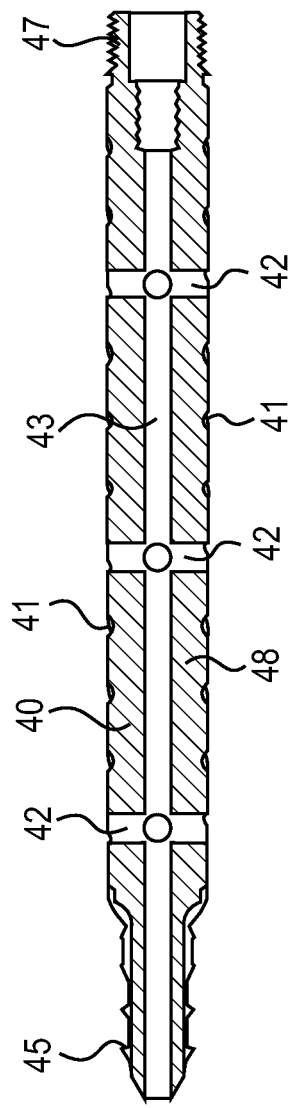
FIG. 4 is a sectional view of a beam similar to, but shorter than, the beam shown in FIG. 3.

FIG. 4 is a side cross-sectional view of an alternative example of a beam 40 that is very similar to beam 30, only it is shorter in length. Beam 40 includes an outside surface 48 having groove 41 cut into it. There are holes 42 shown that communicate between the chamber 43 and the top and bottom of the beam 40 as well as on the back side (not shown) of the beam 40. In this configuration, holes 42 extend from the chamber 43 outwardly through the beam 40 on four sides at equidistant lengths along beam. As noted earlier, these holes 42 could alternatively be placed other distances apart, including asymmetrically, to make the holes 42 customized for where a therapeutic agent could be delivered. The beam 40 also includes a tip end 45 and a cap end 47.

Figure 5A:
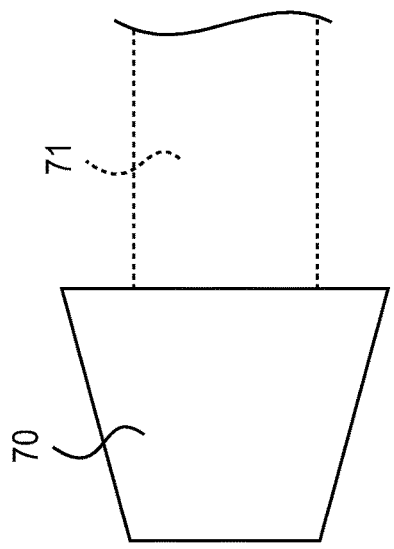
FIGS. 5A and 5B are side elevation views of alternative beam end caps.
Figure 5B:
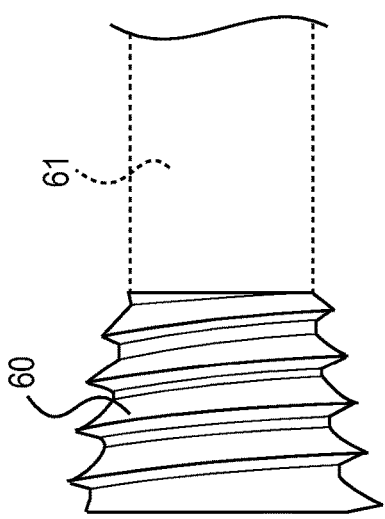

Turning now to FIGS. 5A and 5B, there is shown alternative end cap constructions 60 and 70. The alternative constructions may be placed on the cap ends 37 (FIG. 3) or 47 (FIG. 4) the same as cap 39 as shown in FIG. 2. The cap 60 is a tapered, threaded cap design that flares outwardly from the body of the beam 61 shown in broken lines. Alternatively, a flared cap 71 is shown in FIG. 5B attached to the body of the beam 71 in an opposite orientation from the cap 60 shown in FIG. 5A. Each of these cap constructions 39, 60 and 70 has specific purposes. Other end caps may be engineered for still further therapeutic purposes.

Figure 6:
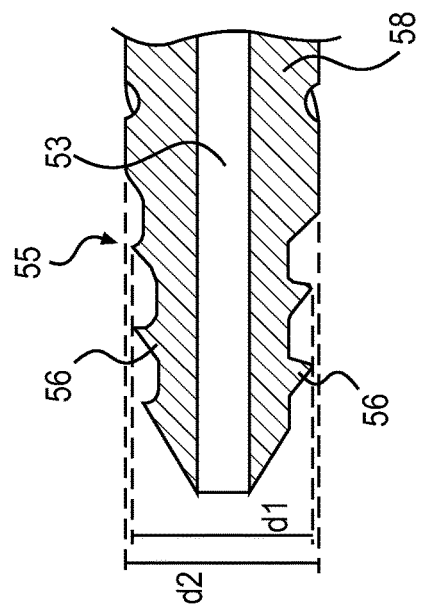
FIG. 6 is a side cross-sectional view of a distal tip end of a beam insert in accordance with the present invention.

In FIG. 6, the tip end 55 of a beam is shown. The tip end includes the chamber 53 that is in the hollow center of a beam. The tip end 55 includes threads 56. The diameter d1 of the outside edge of the threads 56 is less than the diameter d2 of the body 58 of the tip end of the beam. In alternative examples, the tip end of a beam may have a diameter substantially equal to the diameter of the body of the beam.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

The invention claimed is:

1. A foot beam insert comprising:
   a monolithic, load-bearing, cannulated beam having a longitudinal axis, the beam comprising a threaded tip end having a first length and, on an opposite end of the beam, a cap end having a third length, and an unthreaded body of the beam between the threaded tip end and the cap end, the unthreaded body having a second length, wherein the second length is greater than the first length and the third length and comprises a majority of the beam length;
   the unthreaded body of the beam including a groove helically arranged around and cut in an outside surface of the unthreaded body and terminating proximally of the threaded tip end, the groove being shallower and narrower than roots of threads of said threaded tip end such that the outside surface is substantially smooth outside of said groove and the unthreaded body is adapted to support a weight of a patient;
   wherein from a side view, a crest of said threads of said threaded tip end creates a first slope with said longitudinal axis and a root of said groove creates a second slope with said longitudinal axis, wherein said second slope is steeper than said first slope;
   wherein a distance between adjacent roots of said groove is greater than a distance between adjacent crests of said threads of said threaded tip end;
   wherein said threads of said threaded tip end of the beam have a first outside diameter, said unthreaded body of the beam has a second outside diameter extending over substantially the entire second length of said unthreaded body, and said cap end has a third outside diameter, wherein said second outside diameter is greater than said first outside diameter and said second outside diameter is greater than said third outside diameter, wherein said second outside diameter is greater than a diameter of any portion of said cap end, wherein said second outside diameter is greater than said first outside diameter of any portion of said threads, and wherein said second outside diameter is greater than or substantially equal to an outside diameter of any other portion of said cannulated beam; and
   wherein the unthreaded body of the beam defines a hollow chamber therein and the unthreaded body of the beam comprises holes through the unthreaded body of the beam that communicate between the chamber and the outside surface of the unthreaded body.

2. The foot beam insert as claimed in claim 1, wherein the groove has a fluted edge thereon.

3. The foot beam insert as claimed in claim 1, wherein the beam is cylindrical in shape.

4. A kit comprising the foot beam insert as claimed in claim 1, and an end cap, said end cap being attachable to said cap end to cover a proximal end of said cap end, said end cap comprising a fourth outside diameter, wherein said fourth outside diameter is greater than said third outside diameter.

5. The kit of claim 4, wherein said end cap is fixed to said cap end, wherein said end cap caps a proximal end of said hollow chamber.

6. The kit of claim 5, wherein said end cap flares outwardly from an end of said end cap nearer said unthreaded body of the beam to an end of said end cap further from said unthreaded body of the beam.

7. The kit of claim 5, wherein said end cap flares outwardly from an end of said end cap further from said unthreaded body of the beam to an end of said end cap nearer said unthreaded body of the beam.

8. The kit of claim 5, wherein said end cap is externally threaded.

9. The foot beam insert as claimed in claim 1, wherein the beam is comprised of stainless steel.

10. The foot beam insert of claim 1, wherein said foot beam insert has a length of about 110 mm and said second outside diameter is about 7.3 mm.

* * * * *